United States Patent
Gündel et al.

(10) Patent No.: US 7,933,436 B2
(45) Date of Patent: Apr. 26, 2011

(54) APPARATUS FOR AUTOMATICALLY DETECTING SALIENT FEATURES IN MEDICAL IMAGE DATA

(75) Inventors: Lutz Gündel, Erlangen (DE); Daniel Rinck, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1300 days.

(21) Appl. No.: 11/498,799

(22) Filed: Aug. 4, 2006

(65) Prior Publication Data
US 2007/0031016 A1  Feb. 8, 2007

(30) Foreign Application Priority Data
Aug. 5, 2005 (DE) .................. 10 2005 036 998

(51) Int. Cl.
G06K 9/00 (2006.01)
G06K 9/62 (2006.01)
G06K 9/46 (2006.01)
A61B 5/103 (2006.01)
G09G 5/00 (2006.01)

(52) U.S. Cl. ........ 382/128; 382/159; 382/190; 600/587; 128/897; 345/581

(58) Field of Classification Search .......... 382/128–131, 382/159, 190; 345/581, 625; 600/407, 587
See application file for complete search history.

(56) References Cited

U.S. PATENT DOCUMENTS

| | | | |
|---|---|---|---|
| 5,235,510 A * | 8/1993 | Yamada et al. | 600/300 |
| 6,169,817 B1 * | 1/2001 | Parker et al. | 382/131 |
| 6,171,246 B1 * | 1/2001 | Averkiou et al. | 600/458 |
| 6,628,743 B1 * | 9/2003 | Drummond et al. | 378/8 |
| 7,052,461 B2 * | 5/2006 | Willis | 600/443 |
| 7,095,890 B2 * | 8/2006 | Paragios et al. | 382/173 |
| 7,110,616 B2 * | 9/2006 | Ditt et al. | 382/284 |

(Continued)

FOREIGN PATENT DOCUMENTS
WO  WO 2004/029851 A1  4/2004

OTHER PUBLICATIONS

Willi A.Kalender: "Computertomographie—Grundlagen, Gerätetechnologie, Bildqualität, Anwendungen", Publicis MCD Werbeagentur, 2000, pp. 147-171, ISBN: 3895780820.

(Continued)

Primary Examiner — Bhavesh M Mehta
Assistant Examiner — Mia M Thomas
(74) Attorney, Agent, or Firm — Harness, Dickey & Pierce, P.L.C.

(57) ABSTRACT

An apparatus is disclosed for automatically detecting salient features in medical image data. The apparatus includes a memory device for storing the image data, at least one determination module for determining one or more anatomical regions which are acquired by the image data, a number of different examination modules that respectively include an application for automatically detecting specific salient features in a specific anatomical region, an input unit via which a primary application can be started, a control unit that on the basis of the anatomical regions determined by the determination module automatically selects and executes in the background further applications, as well as an output unit on which the result of the primary application is displayed together with an item of information relating to additional salient features that have been detected automatically with the aid of the applications executed in the background. The apparatus improves the diagnostic evaluation of medical image data.

11 Claims, 1 Drawing Sheet

U.S. PATENT DOCUMENTS

| | | | |
|---|---|---|---|
| 7,297,111 B2* | 11/2007 | Iliff | 600/300 |
| 7,310,651 B2* | 12/2007 | Dave et al. | 707/104.1 |
| 7,346,203 B2* | 3/2008 | Turek et al. | 382/131 |
| 7,403,811 B2* | 7/2008 | Sathyanarayana | 600/424 |
| 7,460,051 B2* | 12/2008 | Nasvall et al. | 342/7 |
| 7,490,085 B2* | 2/2009 | Walker et al. | 707/10 |
| 7,536,042 B2* | 5/2009 | Murphy et al. | 382/128 |
| 7,599,542 B2* | 10/2009 | Brockway et al. | 382/132 |
| 7,620,227 B2* | 11/2009 | Gering et al. | 382/128 |
| 7,646,901 B2* | 1/2010 | Murphy et al. | 382/128 |
| 7,720,520 B2* | 5/2010 | Willis | 600/424 |
| 7,756,358 B2* | 7/2010 | Deng et al. | 382/294 |
| 2002/0097902 A1* | 7/2002 | Roehrig et al. | 382/132 |
| 2003/0078485 A1* | 4/2003 | Hartlep | 600/378 |
| 2003/0161522 A1* | 8/2003 | Campanini et al. | 382/132 |
| 2004/0022425 A1* | 2/2004 | Avinash et al. | 382/131 |
| 2004/0184646 A1* | 9/2004 | Oosawa | 382/128 |
| 2004/0223633 A1* | 11/2004 | Krishnan | 382/128 |
| 2005/0008205 A1* | 1/2005 | Kiraly et al. | 382/128 |
| 2005/0013471 A1* | 1/2005 | Snoeren et al. | 382/131 |
| 2005/0100208 A1* | 5/2005 | Suzuki et al. | 382/157 |
| 2005/0113961 A1* | 5/2005 | Sabol et al. | 700/182 |
| 2005/0152589 A1* | 7/2005 | Wehnes et al. | 382/128 |
| 2005/0197567 A1* | 9/2005 | Qian et al. | 600/425 |
| 2006/0173271 A1* | 8/2006 | Shen et al. | 600/407 |
| 2006/0173272 A1* | 8/2006 | Qing et al. | 600/407 |
| 2007/0201735 A1* | 8/2007 | Gundel | 382/128 |
| 2007/0242901 A1* | 10/2007 | Huang et al. | 382/294 |

OTHER PUBLICATIONS

D.A.Bluemke et al.: << Spiral CT Evaluation of Liver Tumors >>, in : Spiral CT : Principles, Techniques and Clinical Applications, 1995, Chapter 3, pp. 25-43.

R.Felix, M.Langer: "Advances in CT II", Springer Verlag, Mar. 1992, pp. 109-115, pp. 126-130, ISBN: 3540554025.

H.Pokieser, G.Lechner: "Advances in CT III", Springer Verlag, Apr. 1994, pp. 276-283, ISBN: 3540581987.

G.P.Krestin, G.M.Glazer: "Advances in CT IV", Springer Verlag, Mar. 1998, pp. 165-170, pp. 196-208, ISBN: 3540643486.

* cited by examiner

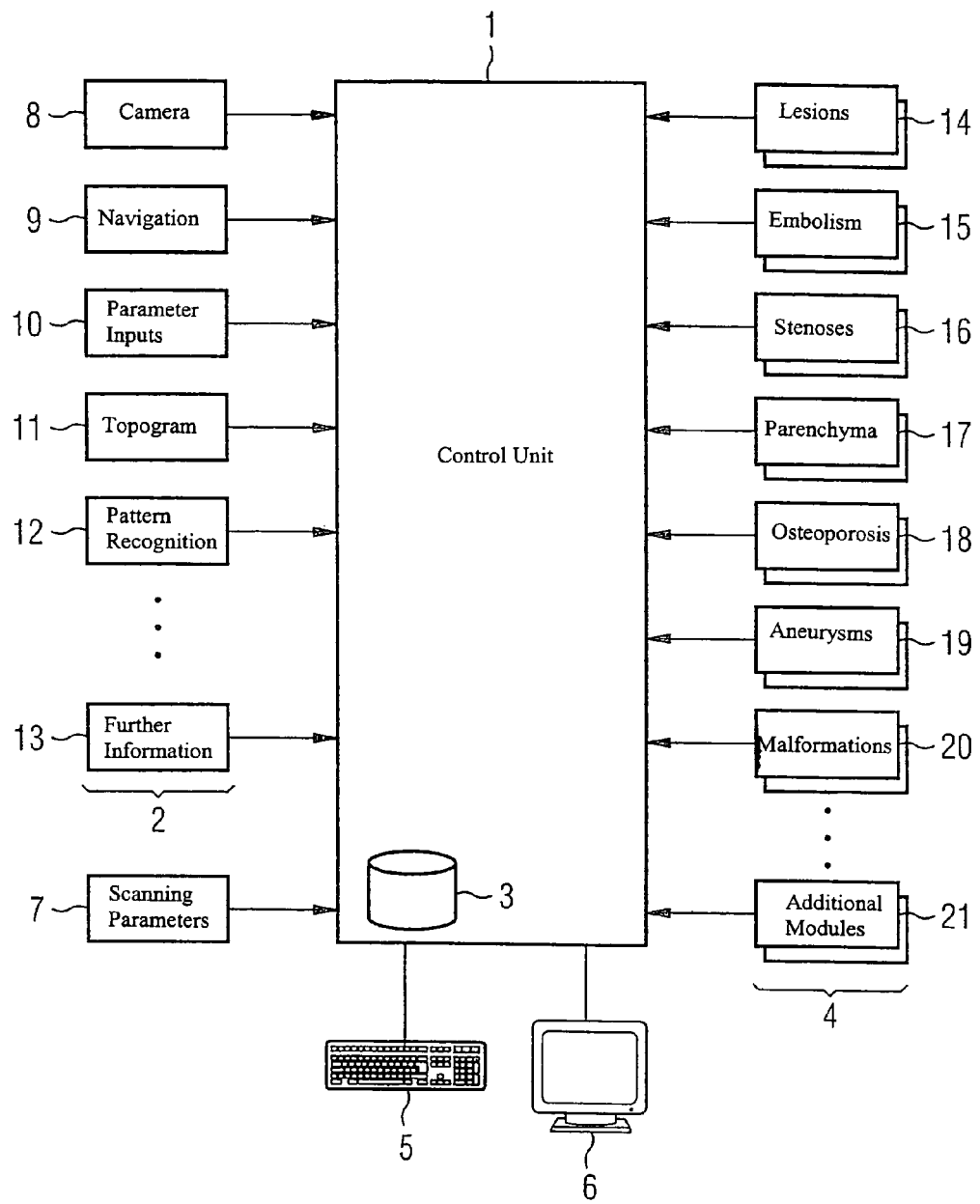

APPARATUS FOR AUTOMATICALLY DETECTING SALIENT FEATURES IN MEDICAL IMAGE DATA

PRIORITY STATEMENT

The present application hereby claims priority under 35 U.S.C. §119 on German patent application number DE 10 2005 036 998.7 filed Aug. 5, 2005, the entire contents of which is hereby incorporated herein by reference.

FIELD

The present invention generally relates to an apparatus. For example, it may relate to one for automatically detecting salient features in medical image data of a body area of a patient, having a memory device for storing the image data, an input unit with the aid of which an application for automatically detecting specific salient features in the image data can be started, as well as an output unit on which the result of the application is displayed.

BACKGROUND

Medical imaging is used in the most varied diagnostic problems in order to support the diagnosis for a patient. It is true that diagnostically relevant salient features can be detected by an experienced user in the recorded image data, but with users who are still inexperienced there is the risk of such salient features being overlooked because of an image quality that is not always optimal. Known for the purpose of ameliorating this problem are apparatuses with the aid of which it is possible for salient features in the recorded image data to be detected automatically. These apparatuses generally comprise a data processing station having a memory for the image data on which the user can start a CAD application (CAD: Computer Aided Detection). Thus, for example, applications are known for automatically detecting lesions in the anatomical regions of thorax, lung and large intestine. Further known applications concern the liver, the bones and the brain.

Once the image data to be evaluated are to hand, the corresponding application is started either automatically or by an input from the user. Different examination modules with the different applications are available for the different diagnostic problems: for example an application for automatically detecting pulmonary nodules in pulmonary diagnostics, or an application for automatically detecting mammary nodules in the case of mammary diagnostics. Other anatomical regions that can also be acquired in diagnostic imaging, or other diagnostic problems are not taken into account in the automatic detection.

SUMMARY

An apparatus is provided, in at least one embodiment, for automatically detecting salient features in medical image data that further reduces the likelihood of unrecognised salient features in medical image data.

The apparatus, for automatic detection in medical image data of a body region of a patient, in at least one embodiment comprises a memory device for storing the image data, an input unit for starting a primary application in order to detect specific salient features in the anatomical target region that correspond to the causal diagnostic problem, as well as an output unit on which the user displays the result of the primary application. In at least one embodiment of the present application, the anatomical region relevant to the diagnostic problem is also denoted as target region, and must, of course, be included by the image data in this case. The primary application is specifically designed for detecting in the target region salient features that correspond to the diagnostic problem. Alternatively, the user can also use the input unit to select a diagnostic problem on the basis of which a suitable primary application is then automatically started.

The apparatus, in at least one embodiment, further comprises a number of examination modules that respectively comprise at least one application for automatically detecting specific salient features in a specific anatomical region. The apparatus is distinguished chiefly by the presence of at least one determination module for determining one or more anatomical regions, acquired by the image data, and of a control unit that, on the basis of at least the anatomical regions determined by the determination module, automatically selects and executes in the background further applications, which are suitable for detecting salient features in the anatomical region(s) acquired by the image data. The determination of the one or more anatomical regions by the determination module is performed via an automatic evaluation of the image data by means of pattern recognition, account preferably being taken of additional data that are fed to the determination module via one or more input interfaces. The information relating to additional salient features that have been automatically detected with the aid of the applications executed in the background is then likewise displayed on the output unit.

Consequently, irrespective of the diagnostic problem prescribed by the user all the applications, available in the apparatus, for automatically detecting salient features that can be applied to the stored image data are started and executed by the present apparatus. Thus, for example, in the case of an examination of the large intestine in the image data it is likewise possible to check the abdomen automatically for salient features and thus to check any possible further findings. The user continues, in a customary manner, to select the primary diagnostic problem, or starts the associated primary application.

The further applications selected by the control unit generally run in the background without being noticed by the user. It is only in the case of detection of a salient feature in the image data by these further applications that the user is informed of a possible positive finding. He can then start further examinations on the present image data record or, if appropriate, prompt a further measure with either the same or another imaging method.

Automatically selecting further applications by way of the control unit requires knowledge of which anatomical regions have been acquired with the image data. The determination module is used to determine these anatomical regions. When making a determination via an automatic evaluation of the image data, it is possible to take account of additional information that is fed to the determination module via one or more corresponding input interfaces. What is involved here can be parameter inputs by the user, or else other information, for example image data of other imaging methods from which the anatomical areas can be determined.

Consequently, the apparatus, in at least one embodiment, automatically detects salient features on the basis of the anatomical region acquired by the medical imaging used, irrespective of the primary diagnostic problem being addressed. The salient features can be, for example, lesions, stenoses, aneurysms, embolisms, pulmonary parenchyma diseases, osteoporosis or anatomic changes. For the user, who generally is chiefly interested in the salient features associated with the diagnostic problem, using the apparatus reduces the risk of unrecognized salient features in the available medical image data. The recorded image data, which frequently also comprise anatomical areas outside the diagnostic problem, in particular areas outside the anatomic target region, can therefore be used optimally in terms of their information content. The user automatically obtains an indication of possible salient findings outside the diagnostic problem. Of course, the same also holds for the detection of salient features in the anatomical target region other than those associated with the diagnostic problem.

The further applications need not run at the same time as the primary application. This holds, in particular, whenever the user does not start the primary application until a later point in time. In this case, the further applications can already be started and executed by the control unit after receipt of the image data, and so the user can already be shown possible findings from the further applications at the start of the primary application. A number of, or all the further applications can be executed simultaneously, that is to say in parallel, or else consecutively.

Any desired combinations are possible here as a function of the applications. Of course, it is advantageous to have available in the apparatus as many examination modules as possible and thus as many different applications as possible for automatically detecting different salient features and/or for automatically detecting salient features in different anatomical regions. The higher the number of examination modules the better the recorded image data are evaluated for possible salient features. Applications for automatically detecting salient features in the anatomical regions of thorax, lung, large intestine, liver, in the bones and in the brain are particularly advantageous in this case. Furthermore, applications should be present for automatic detection in vessels, for example finding blockages, aneurysms and vessel malformations. This also applies to kidney, biliary and bladder stones.

Examples of suitable applications and/or algorithms available to the person skilled in the art straight away are to be found, for example, in Willi A. Kalender, Computertomographie [Computed Tomography], Publicis MCD Werbeagentur, Munich, 2000, ISBN 3-89578-082-0; in Elliot K. Fishman, R. Brooke Jeffrey, Spiral CT, Raven Press New York, 1995; in R. Felix, M. Langer, Advances in CT II, Springer, Berlin, 1992, ISBN 3-540-55402-5; in H. Pokieser, G. Lechner, Advances in CT III, Springer, Berlin, 1994, ISBN 3-540-58198-7; or in G. P. Krestin, G. M. Glazer, Advances in CT IV, Springer, Berlin, 1998, ISBN 3-540-64348-6, the entire contents of each of which is hereby incorporated herein by reference.

BRIEF DESCRIPTION OF THE DRAWINGS

The present apparatus will be described below once again by way of example with the aid of an example embodiment in conjunction with the drawing.

The FIGURE here shows an example of such an apparatus having a control unit 1, one or more determination modules 2, a memory unit 3 for storing the image data, a number of examination modules 4, an input unit 5 for the user as well as a monitor 6 as output unit.

DETAILED DESCRIPTION OF THE EXAMPLE EMBODIMENTS

Of the examination modules 4 there are to be seen in the present example one examination module with one or more applications for detecting lesions 14, one examination module with one or more applications for detecting embolisms 15, one examination module with one or more applications for detecting stenoses 16, one examination module with one or more applications for detecting a pulmonary parenchyma disease 17, one examination module with one or more applications for detecting osteoporosis 18, one examination module with one or more applications for detecting aneurysms 19, and one examination module with one or more applications for detecting anatomical malformations 20. The reference numeral 21 indicates further examination modules with further applications, if appropriate modules specialized for different body regions or organs.

After the medical image data have been recorded, for example CT image data recorded with the aid of a computer tomograph, the image data are stored in the memory unit 3 of the apparatus. In a first step, the one or more determination module(s) 2 is/are subsequently used to determine the anatomical region or the anatomical regions acquired by the stored image data. In addition to pattern recognition methods 12, use may be made for this purpose of, for example, parameter inputs by the user 10, a topogram 11 compiled with the aid of the computer tomographs, or the information of other imaging methods such as, for example, a television camera 8 that shows the anatomical region acquired by the image data, or a navigation system 9 in the determination module 2. Pattern recognition methods can extract the required information from the stored image data 3 themselves. Reference numeral 13 indicates that the determination of the anatomical regions can also be performed on the basis of further information fed to the determination module 2.

The suitable applications and/or algorithms are selected via the control unit 1 as a function of the anatomical region(s) found by the determination module. Scanning parameters 7 can be used in addition for this selection, particularly in the case of computer tomography. These can be parameters that specify whether the image data has been recorded with the aid of contrast devices/methods or without contrast devices/methods, or whether, for example, the applied dose at all permits a reasonable evaluation for detecting specific salient features. Furthermore, scanning parameters can also influence the applications and/or algorithms themselves, and so the scanning parameters are made available by the control unit to the selected applications.

As shown in the following example, it is possible thereby for very different applications and/or algorithms to be applied to the recorded image data in succession. The following applications result in the case of image data of the thorax area and epigastrium from a CT with the aid of contrast means: searching for pulmonary nodules, searching for nodules of the anatomical organs (liver, kidney, pancreas), searching for bone metastases on the spine and back, searching for aortic aneurysms, searching for stenoses of the coronary arteries, searching for changes in the pulmonary parenchyma, searching for pulmonary embolisms and for osteoporotic changes to the spine. Furthermore, measurements of the cardiac septum and of the ventricles, for example, are also conceivable. These methods operate in the background, that is to say in parallel with the primary application, in this example to search for pulmonary nodules. In the case of a possible positive finding, the user is informed via the output unit 6 so that he can introduce the further measures correspondingly.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for automatically detecting salient features in medical image data of a body area of a patient, comprising:
   a memory device to store the image data;
   at least one determination module including a unit to determine two or more anatomical regions, in the image data, via pattern recognition, the two or more anatomical regions being at least a target anatomical region associated with a diagnostic problem and a first anatomical region outside the target region;
   a number of different examination modules that respectively include at least one application to automatically detect specific salient features in at least one of the anatomical regions;
   an input unit to start one of the applications as a primary application;
   a control unit that, on the basis of the at least two anatomical regions determined by the determination module, is to automatically select and execute further applications, suitable for detecting salient features in the at least two anatomical regions; and
   an output unit to display the result of the primary application together with an item of information relating to additional salient features that have been detected automatically with the aid of the further applications executed.

2. The apparatus as claimed in claim 1, wherein the determination module includes further units for determining the at least two anatomical regions from additional data that is feedible to the determination module via at least one input interface.

3. The apparatus as claimed in claim 1, wherein the control unit is designed such that it takes account of additional information relating to the image data when selecting the applications.

4. The apparatus as claimed in claim 1, wherein the examination modules include applications at least for automatically detecting at least one of lesions, embolisms, stenoses, pulmonary parenchyma diseases, osteoporosis, aneurysms and anatomic malformations.

5. The apparatus as claimed in claim 2, wherein the control unit is designed such that it takes account of additional information relating to the image data when selecting the applications.

6. The apparatus as claimed in claim 2, wherein the examination modules include applications at least for automatically detecting at least one of lesions, embolisms, stenoses, pulmonary parenchyma diseases, osteoporosis, aneurysms and anatomic malformations.

7. The apparatus as claimed in claim 3, wherein the examination modules include applications at least for automatically detecting at least one of lesions, embolisms, stenoses, pulmonary parenchyma diseases, osteoporosis, aneurysms and anatomic malformations.

8. An apparatus for automatically detecting salient features in medical image data of a body area of a patient, comprising:
   memory means for storing the image data;
   at least one determination module including means for determining two or more anatomical regions, in the image data, via pattern recognition, the two or more anatomical regions being at least a target anatomical region associated with a diagnostic problem and a first anatomical region outside the target region;
   a number of different examination modules that respectively include at least one means for automatically detecting specific salient features in at least one of the anatomical regions;
   an input unit to start one of the applications as a primary application;
   control means for, on the basis of the at least two anatomical regions determined by the determination module, automatically selecting and executing further applications, suitable for detecting salient features in at least two anatomical regions; and
   output means for displaying the result of the primary application together with an item of information relating to additional salient features that have been detected automatically with the aid of the further applications executed.

9. The apparatus as claimed in claim 8, wherein the determination module includes further means for determining the at least two anatomical regions from additional data that is feedible to the determination module via at least one input interface.

10. The apparatus as claimed in claim 8, wherein the control means is designed such that it takes account of additional information relating to the image data when selecting the applications.

11. The apparatus as claimed in claim 8, wherein the examination modules include applications at least for automatically detecting at least one of lesions, embolisms, stenoses, pulmonary parenchyma diseases, osteoporosis, aneurysms and anatomic malformations.

* * * * *